(12) United States Patent
Yeo

(10) Patent No.: US 12,121,355 B2
(45) Date of Patent: Oct. 22, 2024

(54) SYSTEMS AND METHODS FOR MEASURING STRESS LEVELS

(71) Applicant: Georgia Tech Research Corporation, Atlanta, GA (US)

(72) Inventor: Woon-Hong Yeo, Atlanta, GA (US)

(73) Assignee: Georgia Tech Research Corporation, Atlanta, GA (US)

(*) Notice: Subject to any disclaimer, the term of this patent is extended or adjusted under 35 U.S.C. 154(b) by 1 day.

(21) Appl. No.: 17/587,353

(22) Filed: Jan. 28, 2022

(65) Prior Publication Data

US 2022/0151528 A1    May 19, 2022

Related U.S. Application Data

(63) Continuation of application No. 17/346,778, filed on Jun. 14, 2021, now abandoned.

(60) Provisional application No. 63/038,998, filed on Jun. 15, 2020.

(51) Int. Cl.
*A61B 5/16* (2006.01)
*A61B 5/00* (2006.01)
*A61B 5/01* (2006.01)
*A61B 5/0533* (2021.01)

(52) U.S. Cl.
CPC ............ *A61B 5/165* (2013.01); *A61B 5/0004* (2013.01); *A61B 5/01* (2013.01); *A61B 5/0533* (2013.01); *A61B 5/681* (2013.01); *A61B 5/6826* (2013.01); *A61B 5/6898* (2013.01); *A61B 5/7278* (2013.01); *A61B 5/742* (2013.01); *A61B 2560/0223* (2013.01); *A61B 2560/0431* (2013.01); *A61B 2562/0209* (2013.01); *A61B 2562/164* (2013.01)

(58) Field of Classification Search
CPC ......... A61B 5/165; A61B 5/0004; A61B 5/01; A61B 5/0533; A61B 5/681; A61B 5/6826; A61B 5/6898; A61B 5/7278; A61B 5/742; A61B 2560/0223; A61B 2560/0431; A61B 2562/0209; A61B 2562/164
USPC ....................................................... 600/301
See application file for complete search history.

(56) References Cited

U.S. PATENT DOCUMENTS

2013/0333094 A1* 12/2013 Rogers ................... A61B 34/76
340/407.1
2014/0288401 A1* 9/2014 Ouwerkerk .......... A61B 5/7278
600/345

(Continued)

*Primary Examiner* — Eric J Messersmith
*Assistant Examiner* — Chanel J Jhin
(74) *Attorney, Agent, or Firm* — Troutman Pepper Hamilton Sanders LLP; Ryan A. Schneider; Dustin B. Weeks

(57) ABSTRACT

An exemplary embodiment of the present disclosure provides a method of determining stress levels in a user comprising: receiving galvanic skin response (GSR) measurements by a wearable sensor on the user over a period of time; receiving temperature measurements by the wearable sensor on the user over the period of time; determining changes in the temperature over a predetermined threshold in the temperature measurements over the period of time; calibrating the GSR measurements based on the determined changes in temperature over the predetermined threshold; calculating a stress level of the user based on the calibrated GSR measurements; and generating an output indicative of the calculated stress level.

16 Claims, 13 Drawing Sheets

(56) References Cited

U.S. PATENT DOCUMENTS

| | | | |
|---|---|---|---|
| 2016/0015280 A1* | 1/2016 | Hyde | A61B 5/45 |
| | | | 600/595 |
| 2016/0374588 A1* | 12/2016 | Shariff | A61B 5/0533 |
| | | | 600/547 |
| 2017/0339484 A1* | 11/2017 | Kim | A61B 5/165 |
| 2018/0249939 A1* | 9/2018 | Huang | A61B 5/165 |
| 2018/0310879 A1* | 11/2018 | Chan | A61B 5/4884 |

* cited by examiner

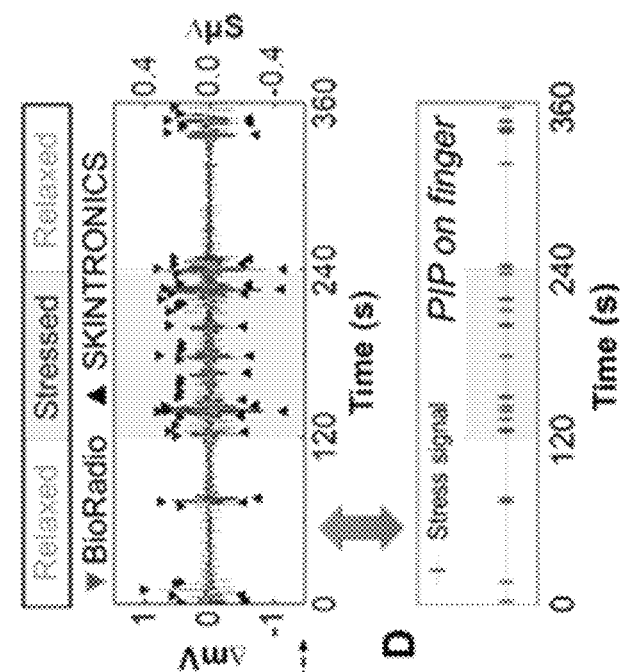
FIG. 3A
FIG. 3B
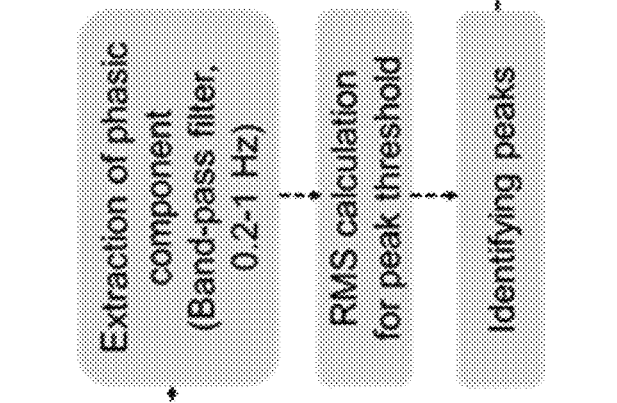
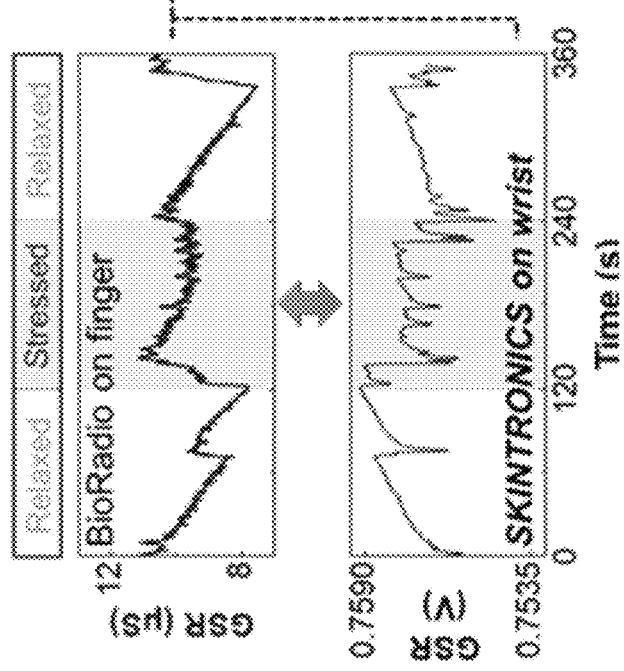
FIG. 3C
FIG. 3D

SYSTEMS AND METHODS FOR MEASURING STRESS LEVELS

CROSS-REFERENCE TO RELATED APPLICATIONS

This application is a continuation of U.S. patent application Ser. No. 17/346,778, filed on 14 Jun. 2021, which claims the benefit of U.S. Provisional Application Ser. No. 63/038,998, filed on 15 Jun. 2020, which are incorporated herein by reference in their entireties as if fully set forth below.

GOVERNMENT LICENSE RIGHTS

This invention was made with government support under Agreement No. FA8650-15-2-5401, awarded by the Air Force Research Laboratory. The government has certain rights in the invention.

FIELD OF THE DISCLOSURE

The various embodiments of the present disclosure relate generally to sensors, and more particularly to sensors for detecting stress levels in users.

BACKGROUND

Chronic stress is one of the significant factors causing serious health complications, such as irritability, depression, cardiovascular disease, and Alzheimer's disease. Traditionally, surveys and questionnaires have been widely used to assess stress levels. These, however, are purely subjective. A magnetic resonance imaging (MRI) technique has also been used to measure stress. Although this MRI technique is a quantitative measure, it has major limitations due to its high cost, discrete measurement, and limited availability. Recently, electrodermal activity, the variation in skin conductance and also known as galvanic skin response (GSR), has been of great interest due to the quantifiable measure of sympathetic arousal and cognitive states which are triggered along with various stressors. GSR sensors can monitor stress activities by detecting skin conductance changes that results from the variation of the ionic permeability of sweat gland membranes. Typically, GSR data are measured by gel-covered metal electrodes, mounted at near maximal concentrations of eccrine sweat glands, such as palm of the hand or fingertips. Such measurement system has limitations of device locations that can bother daily activities and motion artifacts caused by wires and gels. Recent advancements in flexible electronics have enabled wireless wearable devices that can be mounted on other locations, including foot, arm, and wrist. However, these devices still rely on rigid metals and multiple electronic components with bulky plastic packaging and prevent the conformal skin-to-device interface, resulting in the use of a tightly worn band or aggressive tapes. Further, these devices still fail to provide accurate measurements of stress levels experienced by users. Accordingly, there is a need for improved techniques for measuring stress levels.

BRIEF SUMMARY

An exemplary embodiment of the present disclosure provides a method of determining stress levels in a user comprising: receiving galvanic skin response (GSR) measurements by a wearable sensor on the user over a period of time; receiving temperature measurements by the wearable sensor on the user over the period of time; determining changes in the temperature over a predetermined threshold in the temperature measurements over the period of time; calibrating the GSR measurements based on the determined changes in temperature over the predetermined threshold; calculating a stress level of the user based on the calibrated GSR measurements; and generating an output indicative of the calculated stress level.

In any of the embodiments disclosed herein, the method can further comprise identifying peaks in the GSR measurements.

In any of the embodiments disclosed herein, identifying peaks in the GSR measurements can comprise: filtering the GSR measurements to obtain phasic GSR signals; and performing a root mean square calculation on the phasic GSR signals.

In any of the embodiments disclosed herein, the method can further comprise identifying peaks in the GSR measurements over a predetermined magnitude as corresponding to an increased level of stress in the user.

In any of the embodiments disclosed herein, calculating the stress level of the user can comprise determining a number of peaks per time period in the calibrated GSR measurements.

In any of the embodiments disclosed herein, the stress level can be proportional to the number of peaks per time period in the calibrated GSR measurements.

In any of the embodiments disclosed herein, receiving the GSR measurements and temperature measurements can comprise receiving the GSR measurements and temperature measurement at a processor in the wearable sensor.

In any of the embodiments disclosed herein, the method can further comprise displaying the output on the wearable sensor.

In any of the embodiments disclosed herein, receiving the GSR measurements and temperature measurements can comprise receiving the GSR measurements and temperature measurement at a remote device from wearable sensor.

In any of the embodiments disclosed herein, the method can further comprise transmitting the GSR measurements from the wearable sensor to the remote device.

In any of the embodiments disclosed herein, the method can further comprise displaying the output on the remote device.

In any of the embodiments disclosed herein, the wearable sensor can comprise at least one mesh-patterned stretchable electrode for measuring GSR of the user.

Another embodiment of the present disclosure provide a method of indicating a level of stress in a user, comprising: obtaining galvanic skin response (GSR) measurements and temperature measurements by a wearable sensor on the user over a period of time; calibrating the GSR measurements based on changes in the temperature measurements over the period of time; calculating a stress level in the user based on the calibrated GSR measurements; and displaying an output of the calculated stress level.

In any of the embodiments disclosed herein, displaying the output of the calculated stress level can comprise displaying the output of the calculated stress level on the wearable sensor.

In any of the embodiments disclosed herein, displaying the output of the calculated stress level can comprise displaying the output of the calculated stress level on a remote device.

In any of the embodiments disclosed herein, obtaining GSR measurements and temperature measurements can comprise: transmitting the GSR and temperature measurements from the wearable sensor to the remote device; and receiving the GSR and temperature measurements at the remote device.

Another embodiment of the present disclosure provides a device for indicating a level of stress in a user, comprising a processor and memory. The memory can comprise instructions that, when executed by the processor, cause the device to: obtain galvanic skin response (GSR) measurements and temperature measurements by a wearable sensor on the user over a period of time; calibrate the GSR measurements based on changes in the temperature measurements over the period of time; and calculate a stress level in the user based on the calibrated GSR measurements.

In any of the embodiments disclosed herein, the device can further comprise a display configured to display the calculated stress level.

In any of the embodiments disclosed herein, the device can be configured as a wearable sensor.

In any of the embodiments disclosed herein, the device can be a smartphone.

These and other aspects of the present disclosure are described in the Detailed Description below and the accompanying drawings. Other aspects and features of embodiments will become apparent to those of ordinary skill in the art upon reviewing the following description of specific, exemplary embodiments in concert with the drawings. While features of the present disclosure may be discussed relative to certain embodiments and figures, all embodiments of the present disclosure can include one or more of the features discussed herein. Further, while one or more embodiments may be discussed as having certain advantageous features, one or more of such features may also be used with the various embodiments discussed herein. In similar fashion, while exemplary embodiments may be discussed below as device, system, or method embodiments, it is to be understood that such exemplary embodiments can be implemented in various devices, systems, and methods of the present disclosure.

BRIEF DESCRIPTION OF THE DRAWINGS

The following detailed description of specific embodiments of the disclosure will be better understood when read in conjunction with the appended drawings. For the purpose of illustrating the disclosure, specific embodiments are shown in the drawings. It should be understood, however, that the disclosure is not limited to the precise arrangements and instrumentalities of the embodiments shown in the drawings.

FIG. 3A provides a comparison of raw GSR data between a commercial device (BioRadio, top) on finger and an exemplary embodiment of the present disclosure referred to as SKINTRONICS on wrist (bottom).

FIG. 3B provides a flow chart to identify phasic signals from the raw GSR, in accordance with an exemplary embodiment of the present disclosure.

FIG. 3C provides a comparison of identified peaks between the BioRadio and SKINTRONICS.

FIG. 3D provides stress peaks measured by a commercial stress tester (PIP) on finger.

DETAILED DESCRIPTION

To facilitate an understanding of the principles and features of the present disclosure, various illustrative embodiments are explained below. The components, steps, and materials described hereinafter as making up various elements of the embodiments disclosed herein are intended to be illustrative and not restrictive. Many suitable components, steps, and materials that would perform the same or similar functions as the components, steps, and materials described herein are intended to be embraced within the scope of the disclosure. Such other components, steps, and materials not described herein can include, but are not limited to, similar components or steps that are developed after development of the embodiments disclosed herein.

Disclosed herein is a wireless, nanomembrane-based wearable sensing device. The device has an exceptionally small form factor for continuous monitoring of stress of the user in daily life. The device can be worn on many parts of the body, such as the wrist or shoulder. Unlike the conventional stress monitors, the device disclosed herein can be ultrathin, lightweight, and highly soft like a human skin, which results in a comfortable, unobtrusive mounting on the skin for continuous stress assessment. The multi-layered, nanostructured device can comprise a pair of skin-conformal thin-film sensors and a stretchable membrane wireless circuit, together integrated on a soft elastomeric membrane. The device can also include a GSR sensor. GSR signals, which are indicative of stress, can fluctuate based on temperature fluctuations. Thus, temperature fluctuations experienced by the user can result in inaccurate stress readings. Accordingly, the device can further comprise one or more temperature sensors. The temperature sensors can be used to calibrate the measured GSR signals and remove any unwanted signal fluctuation caused by skin-temperature change, while the wireless, intimate contact of the entire device on the skin provides negligible motion artifacts.

Figure 1A:
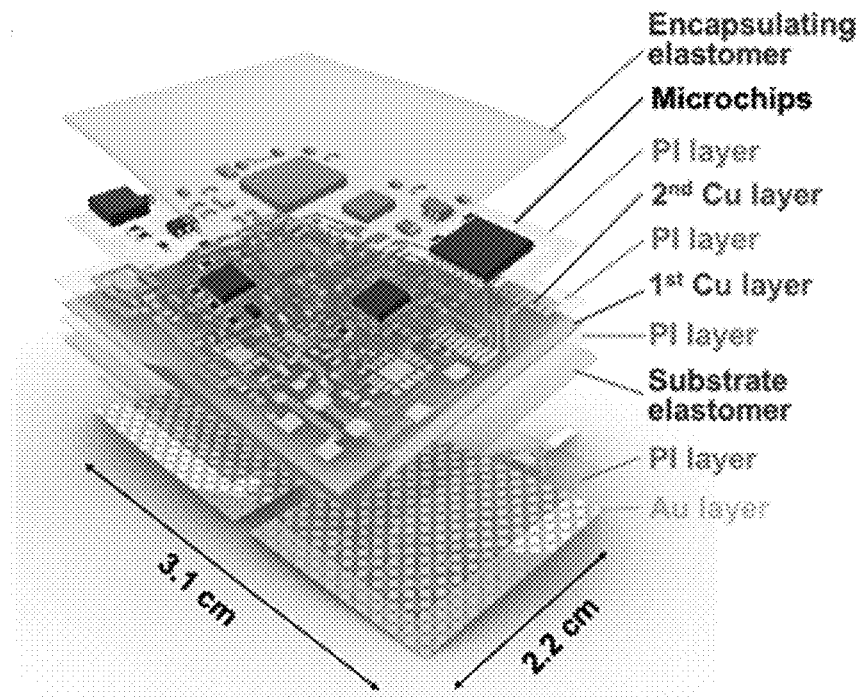
FIG. 1A provides a schematic of an exemplary wearable sensor for monitoring stress levels, in accordance with an exemplary embodiment of the present disclosure.
Figure 1B:
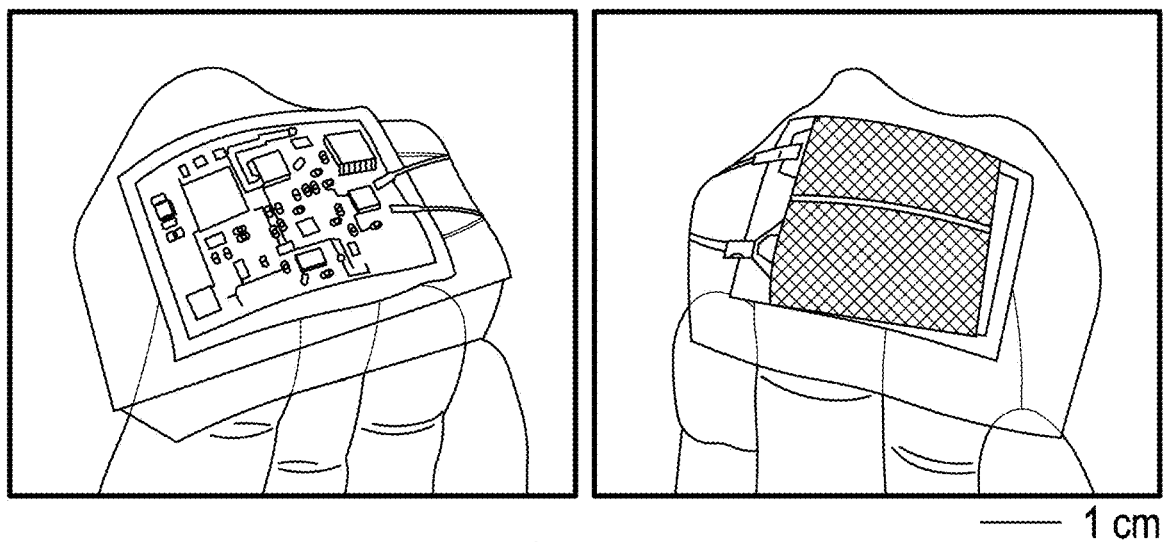
FIG. 1B provides photographs of an exemplary wearable sensor for monitoring stress levels, in accordance with an exemplary embodiment of the present disclosure.
Figure 1C:
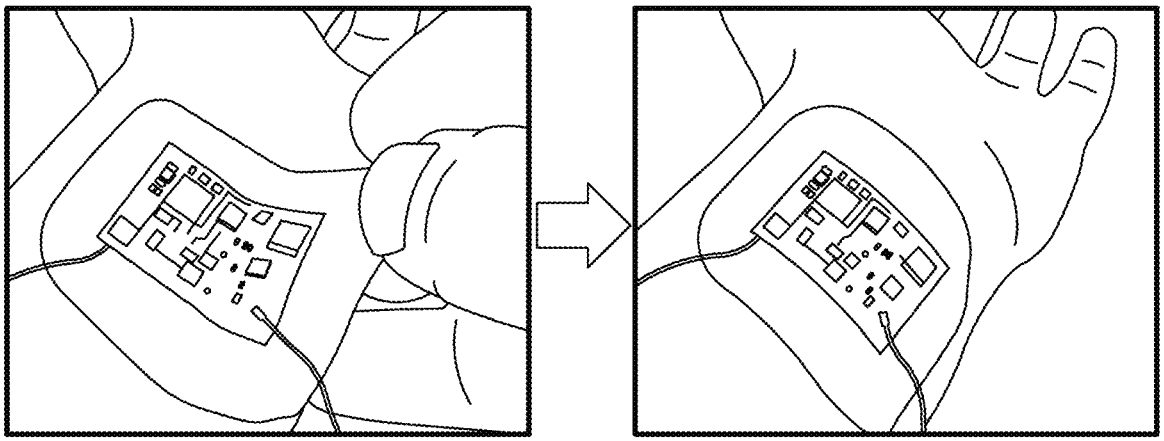
FIG. 1C provides photographs of an exemplary wearable sensor for monitoring stress levels being placed on a user, in accordance with an exemplary embodiment of the present disclosure.

FIG. 1A illustrates the architecture of an exemplary multi-layered wearable device, including a dry, nanomembrane electrode that makes the direct contact to the skin and a stretchable wireless circuit with miniaturized chips for a portable stress monitoring. The device employs a low-modulus elastomer that coats and permeates the device layers to provide natural adhesion to the skin of a wearer as well as to serve as the structural support for the stretchable platform. This allows integrated electrodes in the wearable sensing device to be laminated onto the application site and maintain a robust and conformal adhesion to the body without requiring aggressive adhesives, bandages, or tapes. FIG. 1B provides photograph of an exemplary wearable sensing device that is ultrathin (<5 mm), highly soft (effective moduli <50 kPa), and lightweight (<7 g). The top-view in FIG. 1B shows an elastomer-enclosed stretchable circuit while the bottom-view shows a pair of exposed skin-mounted electrodes. The wireless wearable sensor can make intimate contact to the skin (e.g., wrist) by simply pressing the device with a hand, as shown in FIG. 1C.

Figure 1D:
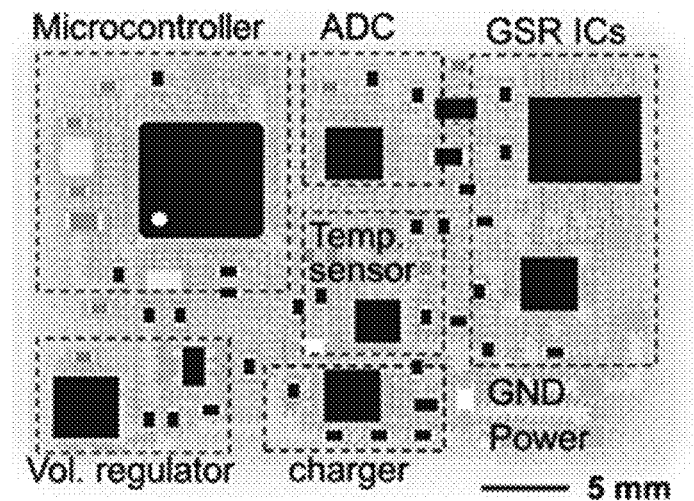
FIG. 1D provides an illustration of a stretchable circuit with multiple electronic components for use on a wearable sensor for monitoring stress, in accordance with an exemplary embodiment of the present disclosure.

FIG. 1D provides an overview of an exemplary electronic circuit design for the wearable sensor, including a GSR integrated circuit, microcontroller, analogue-to-digital converter (ADC), and temperature sensor. The variation of skin conductance of the user can be measured by a pair of electrodes at the bottom side of circuit. A digital potentiometer, linked as a part of the Wheatstone bridge, can actively control the resistance according to a user's skin for sensitive GSR measurement. A digital thermistor (TMP116) can be used to measure the skin temperature with the accuracy of 0.2° C.

Figure 1E:
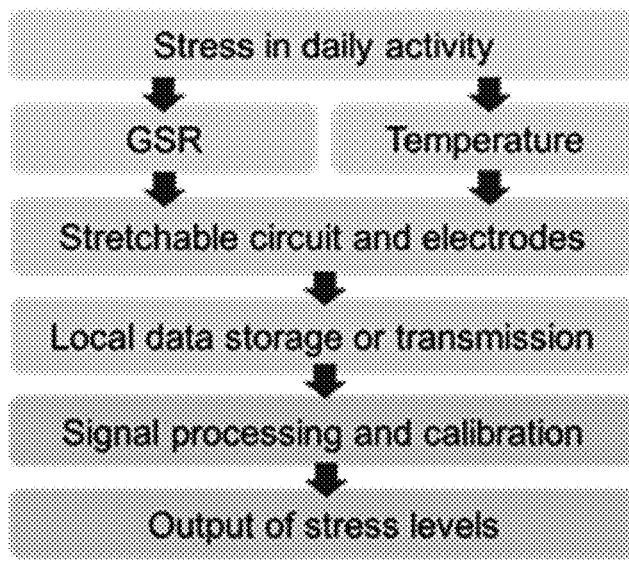
FIG. 1E provides a flow chart of a method of determining stress levels in a user of a wearable sensor, in accordance with an exemplary embodiment of the present disclosure.

FIG. 1E provides a high-level flow diagram of how stress levels can be monitored using the wearable sensor via monitoring of GSR and temperature data. In particular, the user experiences certain stress inducing events. The GSR and temperature signals are recorded by the stretchable circuit worn by the user. Those signal data can be recorded in a memory of the sensor, such as in a flash drive of a microcontroller chip. The signal data can then be extracted later. For example, the signal data can be transmitted (e.g., wirelessly) to a remote device for processing. The GSR signal data can then be processed and calibrated based on effects of the temperature signal data. In other words, to determine accurate stress levels, the temperature sensor can provide information to compensate for an undesired fluctuation of GSR due to the change of body temperature of a user. The calibrated stress levels can then be output. For example, the stress levels can be displayed on a display of the wearable sensor (not shown). The calibrated stress levels can also or alternatively be displayed on the remote device (e.g., a smartphone or other computing device).

Figure 2A:
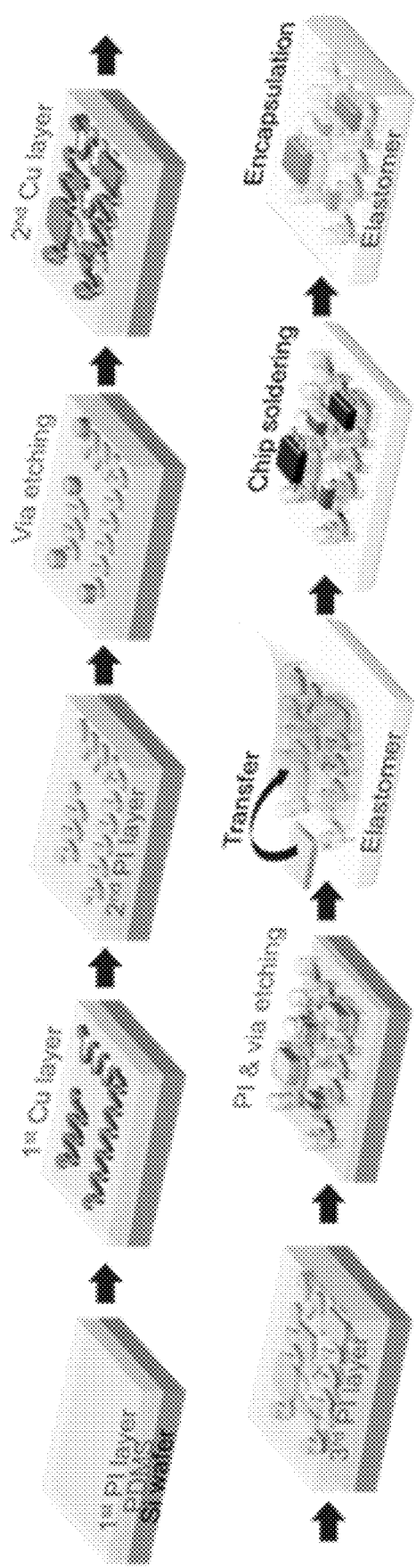
FIG. 2A illustrates an exemplary set of the fabrication steps of a stretchable nanomembrane circuit, in accordance with an exemplary embodiment of the present disclosure.
Figure 2B:
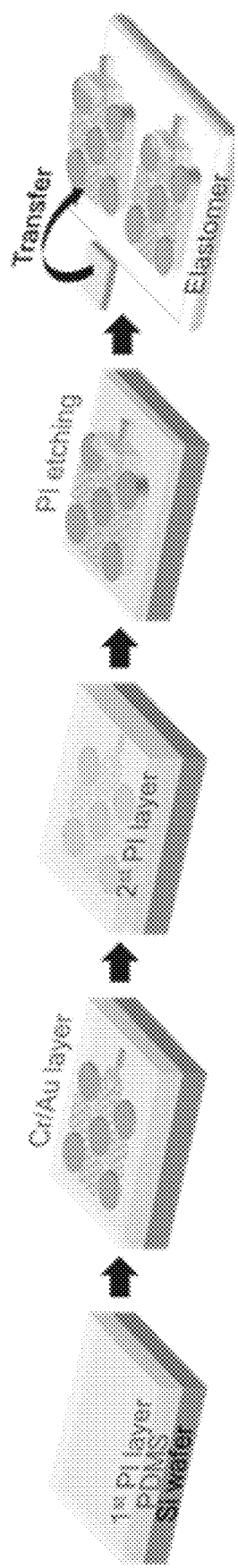
FIG. 2B illustrates an exemplary set of the fabrication steps of a mesh-patterned electrode, in accordance with an exemplary embodiment of the present disclosure.
Figure 2C:
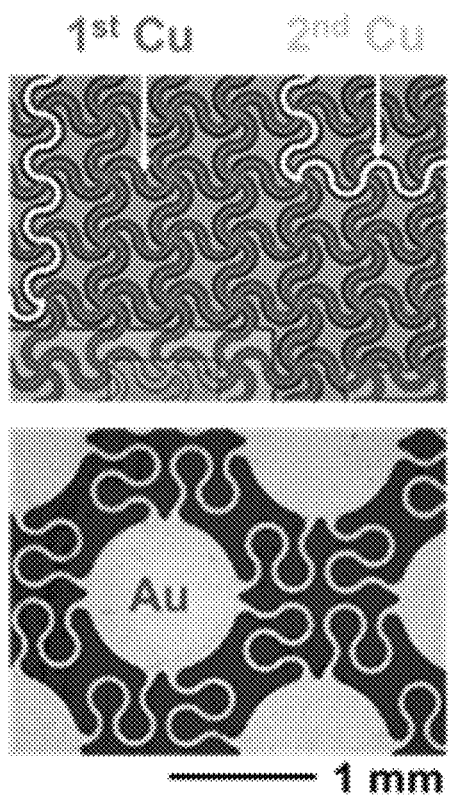
FIG. 2C provides optical microscope images of an open-mesh, stretchable circuit with multi layers (top) and a stretchable electrode (bottom), in accordance with an exemplary embodiment of the present disclosure.
Figure 2D:
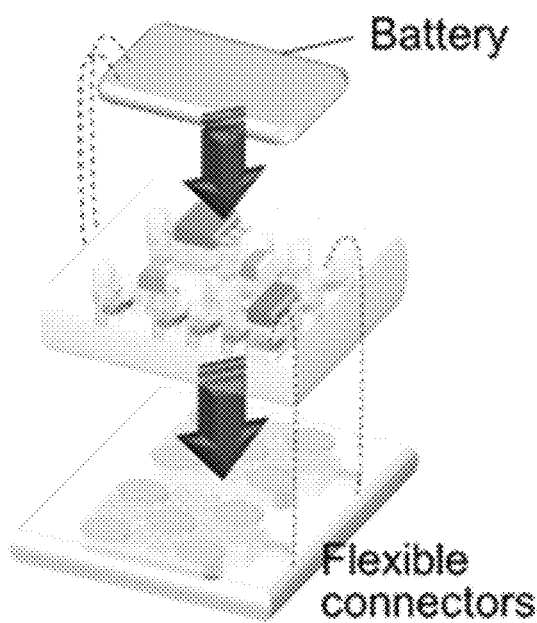
FIG. 2D provides an illustration showing the integration of a pair of electrodes (bottom) with a circuit (middle) and a rechargeable battery (top), in accordance with an exemplary embodiment of the present disclosure.

The accurate capture of GSR provided by embodiments of the present disclosure can be made possible through the use of both a stretchable, wireless circuit as shown in FIG. 2A and a mesh-patterned nanomembrane electrode as shown in FIG. 2B. The wearable sensing device can be fabricated using multiple sequential techniques, including a microfabrication process to construct patterns with photolithography, metallization, transfer printing, and integration of chip components. An exemplary fabrication process is discussed below. The wireless circuit comprises two metal layers for ground plane and chip interconnection (shown at the top of FIG. 2C). The open-mesh, serpentine structure can provide mechanical stretchability to the circuit, while isolating applied strain to the solid chips. An optical microscope picture shown in the bottom of FIG. 2C captures an electrode's pattern, composed of Au islands and meander interconnects, which allows over 50% stretchability and 30% areal coverage to the skin to maintain an adequate contact impedance. The electrodes can be connected to the circuit via a flexible, conductive film, followed by the assembly of a lithium-ion polymer battery with a switch, as shown in FIG. 2D.

Figure 2F:
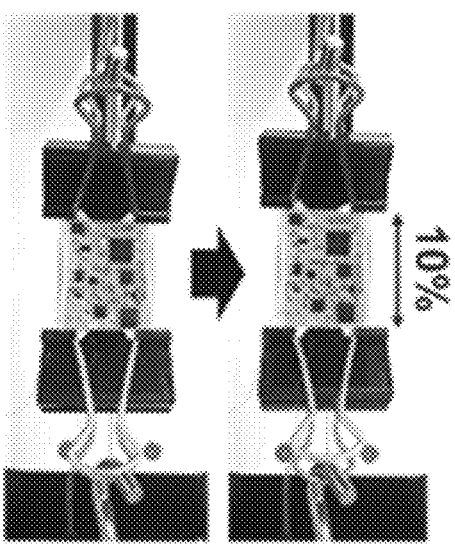
FIG. 2F provides an illustration of the experimental setup for applying a cyclic tensile strain for testing an exemplary embodiment of the present disclosure.
Figure 2G:
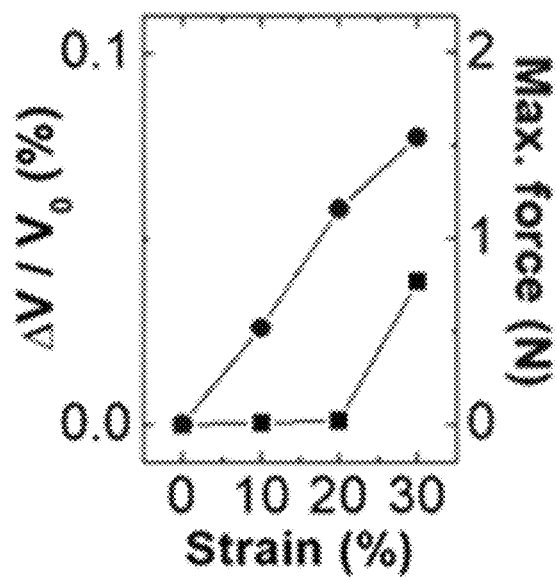
FIG. 2G provides a plot of the electrical measurement of voltage change upon tensile strains, showing negligible change up to 20%, for an exemplary embodiment of the present disclosure.
Figure 2E:
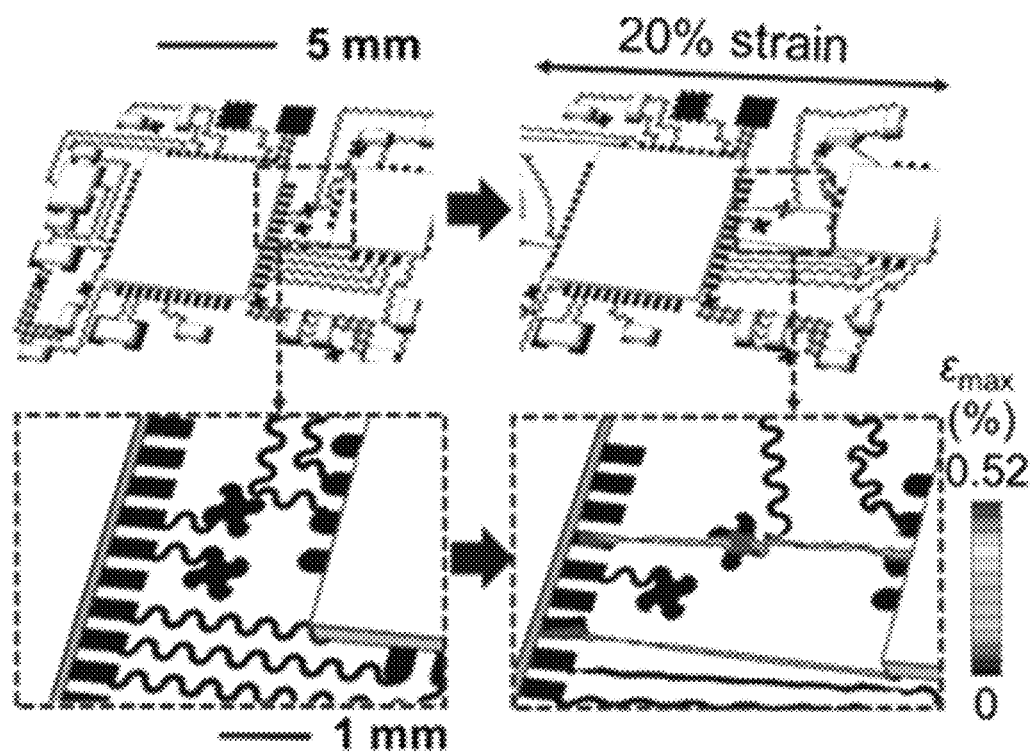
FIG. 2E provides the results of computational mechanics modeling that captures 10% tensile stretching without a mechanical fracture (scale bar: maximum principal strain) for an exemplary embodiment of the present disclosure.
Figure 2H:
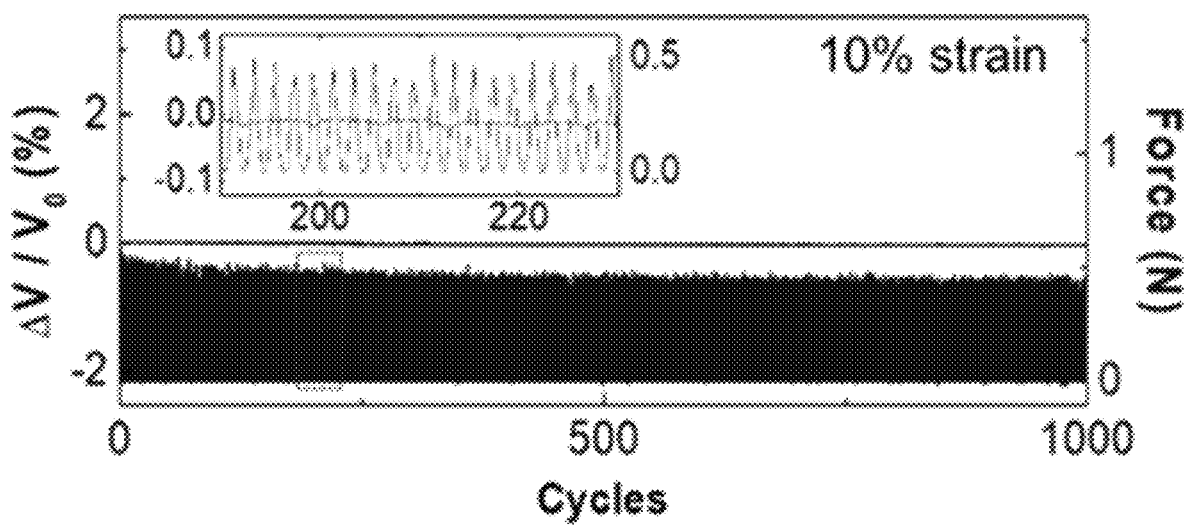
FIG. 2H provides the results of a cyclic mechanical loading for an exemplary embodiment of the present disclosure, showing that 1,000 cycles with 10% tensile strain has a negligible effect, in which the inset shows the magnified view of signals changes during the cyclic loading.

FIG. 2E provides the finite element analysis (FEA) result that estimates an applied tensile strain of 20% and corresponding calculation of the minimal maximum principal strain on Cu interconnects (Cu fracture strain: 5%). An experimental study of mechanical reliability, which is illustrated in FIG. 2F, validates the endurance of the circuit upon cyclic tensile loading. Measured electrical voltage shows negligible changes up to 20% tensile strains, as shown in FIG. 2G, wherein after 20%, a possible deformation occurs on metal interconnects. A cyclic mechanical loading test in FIG. 2H shows the device is stable for at least 1,000 cycles. The mechanical characteristics of the mesh-patterned electrode was validated, showing 30% uniaxial stretchability up to 400 cycles. This structural layout in the electrode and circuit can ensure robust operation at strain levels beyond those that can be tolerated by the skin (10-20%). Accordingly, the device is feasible for practical use in stress monitoring on a user's skin during daily activities. The direct strain from skin deformation will be adsorbed by two layers of the mesh electrode and soft elastomer, which offer minimal transfer of strains to the circuit on top of the device (as shown in FIG. 1A).

GSR, also known as electrodermal activity, is the measure of skin conductance change, caused by human body sweating that is regulated by the autonomic nervous system. Since other factors such as temperature variation and the amount of sweat generation influence the change of GSR, embodiments of the present disclosure monitor both GSR and skin temperature simultaneously. As discussed above, various embodiments of the present disclosure provide more accurate measurement of stress levels indicated by GSR measurements by calibrating GSR measurements with temperature measurements from the user's skin.

An exemplary method of calculating stress levels of a user comprises receiving GSR measurements and temperature measurements from a wearable sensor on the user over the same period of time. These measurements can be transmitted (e.g., wirelessly or by wired connection) from the wearable sensor to a remote device (e.g., a smartphone or other computing device). In some embodiments, the measurements can be transmitted to the remote device in real time. In some embodiments, the measurements can be stored in memory on the wearable sensor for later transmission to the remote device. In some embodiments, the measurements can be received at a processor of the wearable sensor for processing on the wearable sensor.

The method can further comprise identifying peaks in the GSR measurements. The frequency of the peaks (e.g., peaks per minute) correlates to the stress level experienced by the user. Identifying peaks in the GSR measurements can comprise filtering the GSR measurements to obtain phasic GSR signals and performing a root mean square calculation on the phasic GSR signals.

The method can further comprise evaluating the temperature measurements to determine changes greater than a predetermined threshold, as these changes can impact GSR measurements. Temperature changes less than the predetermined threshold can be ignored. The GSR measurements can be calibrated based on the determined changes in temperature over the predetermined threshold. The method can further comprise calculating a stress level of the user based on the calibrated GSR measurements. The stress level can correspond to a number of peaks in the calibrated GSR measurements (higher number of peaks/minute corresponds to higher stress level).

The method can further comprise generating an output indicative of the calculated stress level. In some embodiments, the output can be used to display a stress level on the wearable sensor and/or a remote device.

Fabrication of Exemplary Wearable Sensor

An exemplary method for fabricating a wearable sensing device according to the present disclosure will now be described. The wearable sensing device is referred to herein as "SKINTRONICS." SKINTRONICS comprises two components—nanomembrane stretchable electrodes and stretchable thin-film electronic circuit. Both were developed on a Si wafer spin-coated with polydimethylsiloxane (PDMS)/polyimide (PI) layers. For the circuit, $1^{st}$ Cu layer was deposited and patterned by photolithography, while Cr/Au were used for electrodes. $2^{nd}$ PI layer was coated and etched for interconnection VIA in the circuit, while the PI was etched for creating mesh-patterns for the electrodes. To finish the circuit interconnects, $2^{nd}$ Cu layer was deposited and patterned as like the $1^{st}$ Cu layer, and then $3^{rd}$ PI layer additionally was coated as a protection layer of the exposed Cu layers. The laminated layers of circuit were etched as a serpentine-shaped design and for the position of soldering. The fabricated circuit and electrodes were retrieved from the carrying PDMS/Si wafer by using water-soluble tape (ASWT-2, Aquasol) and placed on a soft silicone elastomer (1:2 mixture of Ecoflex 00-30 and Gels, Smooth-On). Functional microchip components were soldered on the exposed Cu layer followed by the encapsulation of elastomer. A rechargeable lithium-ion polymer battery (110 mAh, LP401230, Adafruit) with a slide switch was connected to the top of circuit. Electrode was attached to the bottom side of the circuit, linking with a flexible conductive film.

Computational Mechanics Modeling with FEA

FEA on the stretchable circuit (SKINTRONICS) was performed by using a simulation software (Abaqus, Dassault Systems). The following material properties were used in the modeling, including $E_{Cu}$=119 GPa and $v_{Cu}$=0.34 for Cu; $E_{PI}$=2.3 GPa and $v_{PI}$=0.34 for polyimide; $E_{SE}$=7.9 kPa and $v_{SE}$=0.49 for silicone elastomer where E is Young's Modulus and v is Poisson's Ratio, respectively.

Experimental Mechanics Study

Cyclic stretching experiment up to 1,000 cycles was conducted to validate the estimated mechanical characteristics from the FEA, while proving the mechanical reliability of the fabricated structures. The circuit clamped on its edge was mounted on a pair of stands. A programmable motorized force gauge (M5-5, Mark-10) applied constant stretching cycles. Thin copper wires were connected between power pads of the device to battery for recording the change of electrical signals during cycles.

Measurement of GSR Data

Raw GSR signals were collected between two mesh-patterned electrodes of SKINTRONICS, attached on the left side of inner wrist and upper trapezius site, which is one of the highly correlated site to finger GSR. To evaluate the quality of data measured by the SKINTRONICS, two commercial devices were utilized, including a clinical-grade physiological monitor, BioRadio, and a portable stress monitor, PIP. To record GSR with the BioRadio, three gel-mounted snap electrodes were attached onto the middle phalanx site of index finger and middle finger, and back of hand as a ground. For the PIP, a subject grabbed two metal plates of the device with fingers as stated by the device instruction, which should maintain the contact throughout the data recording. The recording was conducted in a room with a constant temperature 23±1° C. Overall, the human pilot study involved four healthy volunteers aged 18 to 40.

Quantification of GSR Signals and Motion Artifacts

The phasic components of GSR were extracted from raw data by using the band-pass filter with 0.2 to 1 Hz. RMS value of the phasic signal was calculated as a threshold level to detect peak variations. The peaks shown over the threshold level were defined as an arousal status of stress, counted the number of peaks within one minute. Signal-to-noise ratio (SNR) between the phasic GSR and noise including motion artifacts were separated by using band-pass filter (0.2-1 Hz) and high-pass filter (1 Hz), respectively. RMS value of each signal was calculated, and then put into the following equation, $$SNR(\text{dB}) = 10 \, \text{Log}_{10}\left(\frac{\text{RMS\_signal}}{\text{RMS\_noise}}\right).$$

GSR Wireless and Flash Memory Implementations

A Bluetooth microcontroller (nRF52832, Nordic Semiconductor) was used for data acquisition, storage, and transmission. Two implementations were prepared: 1) for short term monitoring, Bluetooth LE protocol was used to transmit data packets in real time and 2) for long term monitoring, data was stored directly onto the microcontroller's flash memory. Data packets transmitted wirelessly included temperature (16-bit) and GSR data (24-bit), sent in packets of 50 bytes, or 10 datapoints with a connection interval of 200 ms. The sampling rate was set to 5 Hz to track changes over periods of minutes and hours. The capacity of the available flash storage was approximately 262 kB, which could store 12 hours of data at a sampling rate of 1 Hz or 2.4 hours of data at 5 Hz. In terms of power consumption, the flash storage could record data for 7 hours on a 110 mAh Li—Po battery with an average power consumption of 66 mW. In comparison, the Bluetooth LE version depleted in 3.5 hours on the same battery with an average power consumption of 130 mW.

Figure 3E:
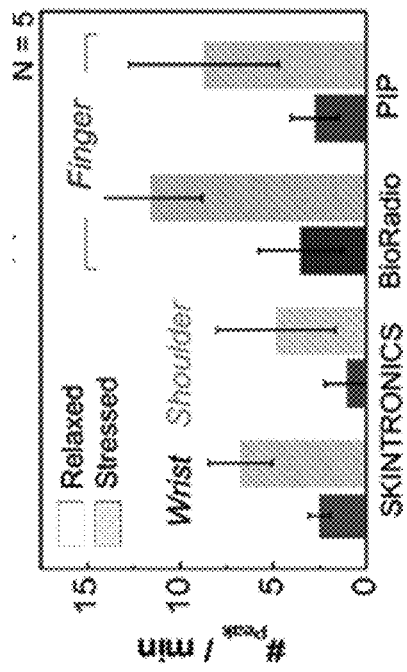
FIG. 3E provides photographs showing three devices to measure GSR simultaneously on wrist and finger (left) and GSR recording with SKINTRONICS on shoulder (left upper trapezius), in which the total weight of each device is 7.0 g (including the battery weight of 2.7 g), 16.5 g, and 134.1 g for SKINTRONICS, PIP, and BioRadio, respectively.
Figure 3F:
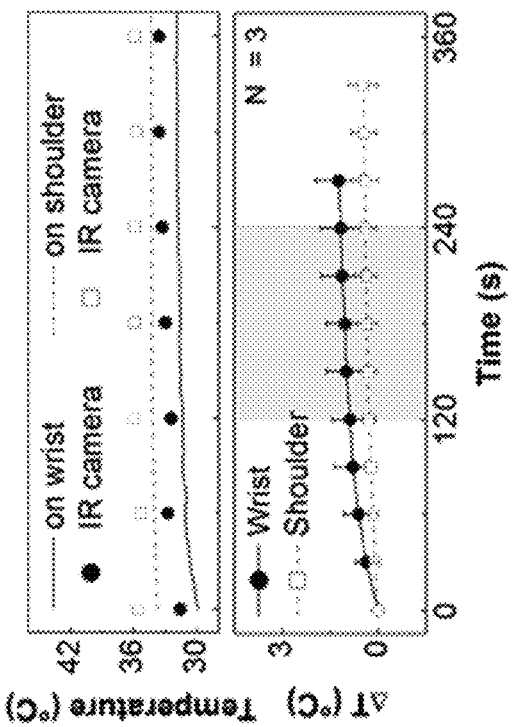
FIG. 3F provides the number of identified stress peaks per minute for the SKINTRONICS, BioRadio, and PIP devices.
Figure 3G:
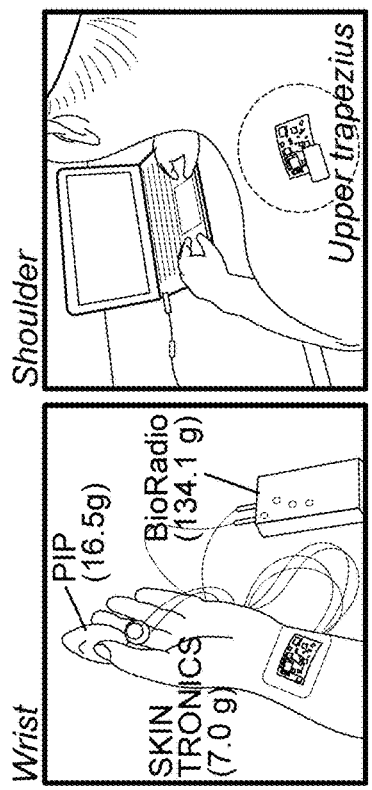
FIG. 3G provides the number of identified stress peaks per minute for the SKINTRONICS (wrist and shoulder) and PIP devices for three subjects.

Characterization of the Device Performance in Comparison with Commercial Devices FIG. 3A provides a comparison of measured GSR data from a commercial device (BioRadio; top graph) and an embodiment of the present disclosure referred to in the figures as "SKINTRONICS" (shown in the bottom graph). The largest difference between the two devices is the locations of electrode placement; BioRadio requires the electrodes to be attached on two fingers, whereas the SKINTRONICS' embedded stretchable electrodes can seamlessly contact other areas, such as the wrist or the upper trapezius (shoulder), which are two of the more desirable positions for measurement of both chronic and acute stress levels. For performance comparison, both devices were simultaneously employed to measure the GSR of a subject under mentally relaxed and stressed states from solving arithmetic problems. For data interpretation (FIG. 3B), raw GSR data were band-passed through frequencies between 0.2 and 1 Hz to extract the phasic component and to reduce the high frequency noise. Next, the distribution of the peaks that are above the root-mean-square (RMS) threshold of the baseline phasic wave was determined. FIG. 3C summarizes the identification of the GSR peaks from both BioRadio and SKINTRONICS, showing the high correlation in the peak distribution. For additional validation, we also compared the measured data with another device (FIG. 3D), namely PIP stress monitor, which is a hand-held, consumer GSR monitoring product. FIG. 3E illustrates the device form factor, mounting location, and weight of all three devices. As can be seen in FIG. 3E, the inventive wearable sensor, i.e., SKINTRONICS, has many advantages over the conventional devices, including minimal weight (about 7 g), compactness, and ability to be worn comfortably on the wrist or the shoulder. Details of GSR data acquired by SKINTRONICS from the shoulder location are shown in FIGS. 4A-D, showing the same peak patterns observed in the two conventional devices. The summary of measured stress peak data from the three devices shows that the SKINTRONICS on the wrist, despite not being attached to the fingers, is still capable of detecting the stressed conditions from three human subjects, where the average number of peaks during the stressed conditions are twice as high or higher as that of the relaxed conditions (shown in FIGS. 3F and 3G). The ratio of the average number of peaks between stressed and relaxed states for SKINTRONICS is 2.69 and 4.83 for the wrist and the shoulder, respectively, which are comparable to BioRadio (3.31) and PIP (3.17). Such differences in the number of peaks are expected since the difference of the sweat gland densities across the fingers, the wrist, and the shoulder contributes to varying levels of GSR data.

Figure 3H:
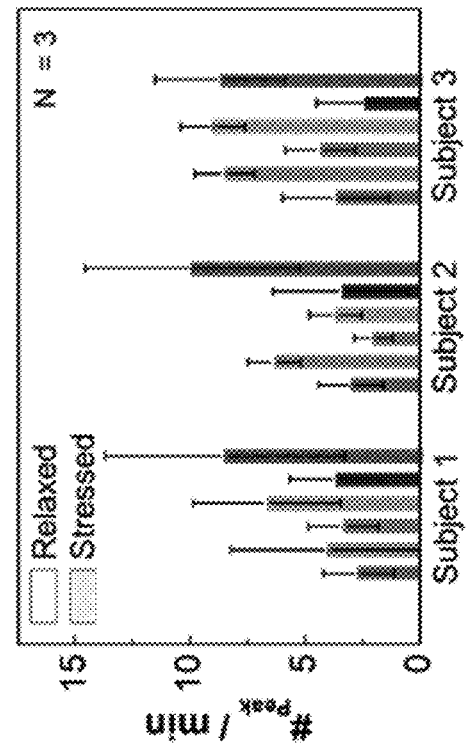
FIG. 3H provides a comparison of temperature recording between SKINTRONICS and an IR camera (top) and temperature deviation during GSR recording on the skin (bottom).
Figure 3I:
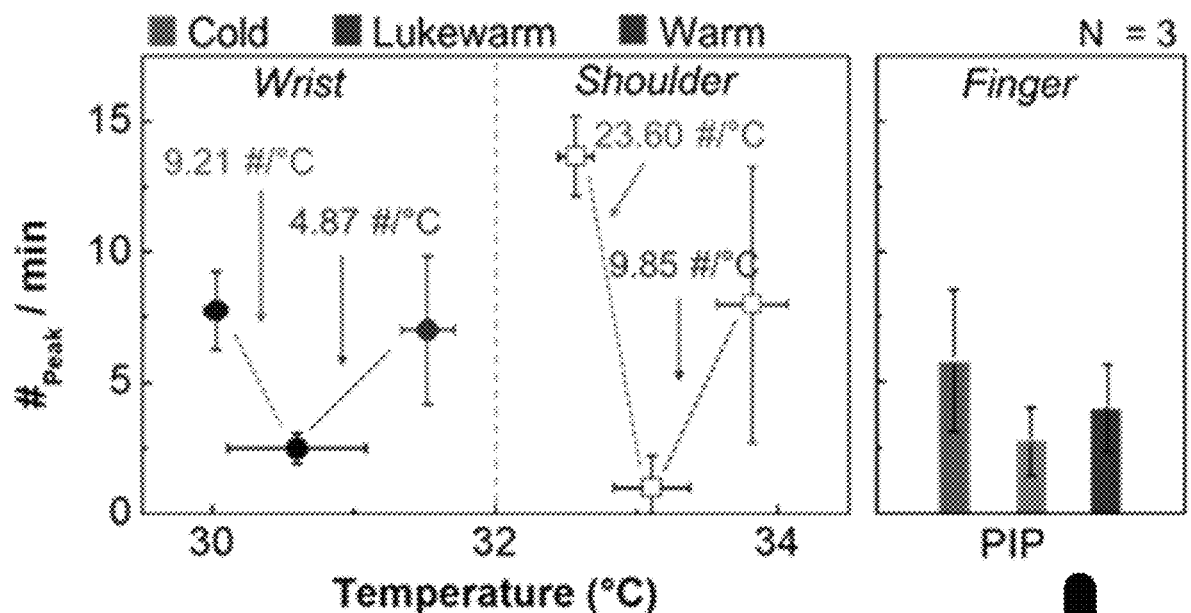
FIG. 3I provides the measured number of stress peaks according to the change of skin temperature without external stress (left) and a calibrated data set on wrist and shoulder (right).
Figure 3I:
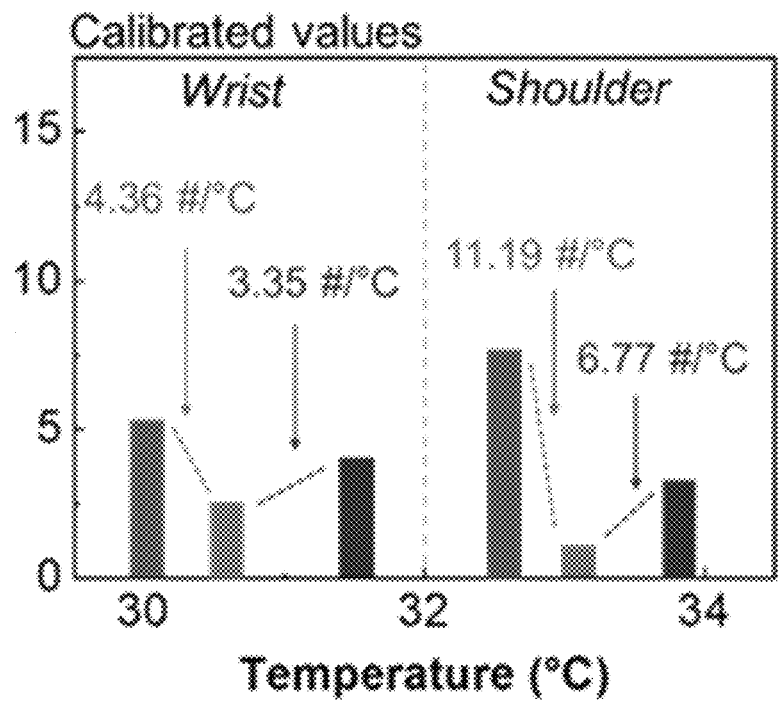
Figure 4A:
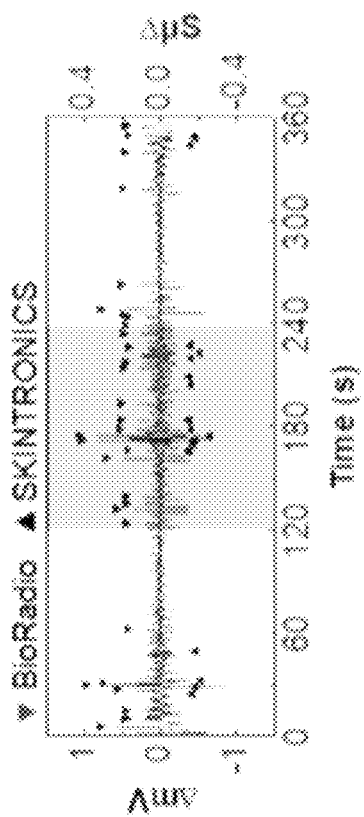
FIG. 4A provides a plot of GSR measurements captured with an exemplary embodiment of the present disclosure (referred to as SKINTRONICS).
Figure 4C:
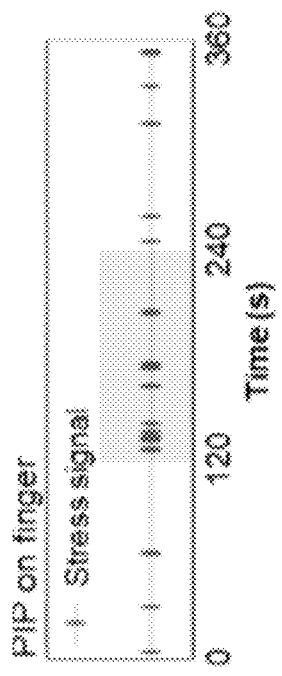
FIG. 4C provides a comparison of peak identifications in GSR measurements from SKINTRONICS and BioRadio.
Figure 4B:
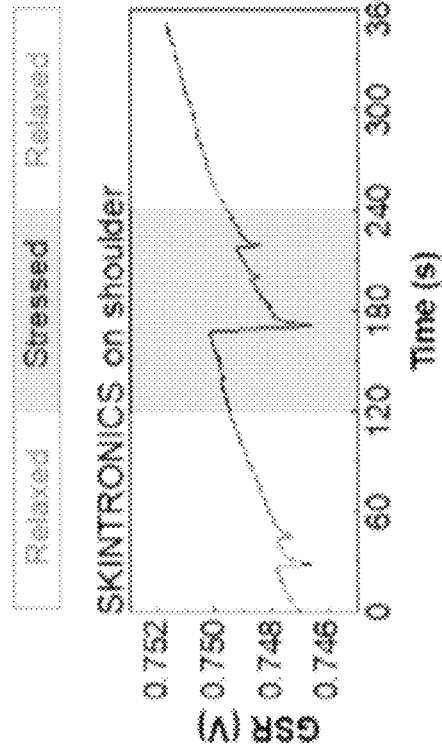
FIG. 4B provides a plot of GSR measurements captured by a conventional device (referred to as BioRadio).
Figure 4D:
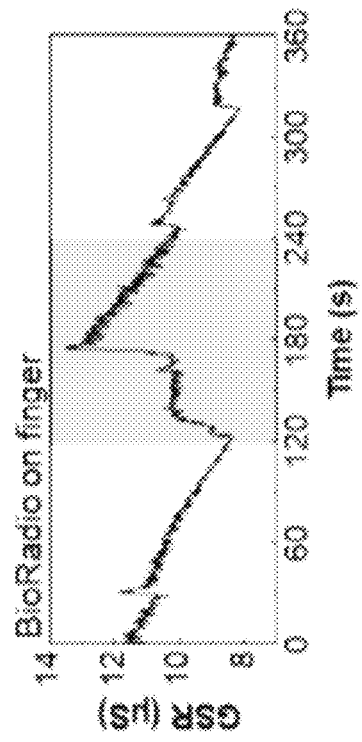
FIG. 4D provides peak identification in GSR measurements from a conventional device (PIP).

Next, the effect of thermoregulation, which is related to the physiological arousal and sweat production, on GSR was investigated using SKINTRONICS. FIG. 3H shows the sensitivity of the skin-wearable device in temperature recording, which is highly comparable to a commercial infrared (IR) camera (E8, FLIR); the deviation between the two devices is ~2° C., which is within the camera's error range (±2° C.). FIG. 3I indicates that the changes in body temperature have an effect on the number of peaks even in the absence of stress and verifies the influence of temperature on the increased phasic GSR components. Furthermore, simultaneous GSR measurements with three devices during relaxed states show that the increase in peak numbers at both cold and warm conditions for SKINTRONICS are significantly higher than those from PIP in FIG. 3I (left). This result suggests that the observed electrodermal activity is a product of complex physiological phenomena that depend not only on the number of sweat glands but also on the body temperature. In order to remove the effect of over-estimation of stress levels, two gradients of the SKINTRONICS data, found at cold and warm temperatures, were calibrated by multiplying with the gradients found in PIP. Finally, the calibrated SKINTRONICS data that consider the effects of both application site and temperature are summarized in FIG. 3I (right).

Assessment of Signal Quality with Body Motions.

Figure 5A:
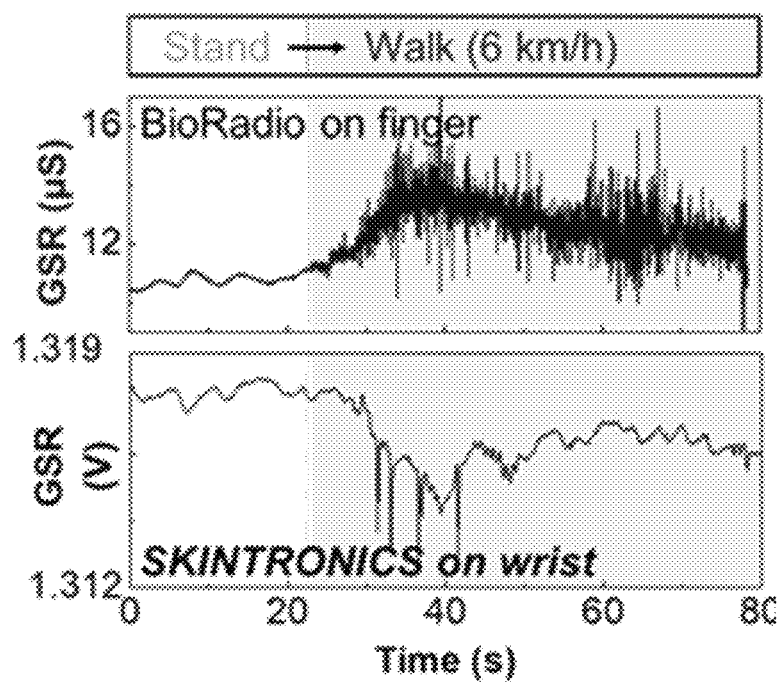
FIG. 5A provides a comparison of raw GSR data measured with BioRadio on finger (top) and SKINTRONICS on wrist (bottom) when a subject walks with 6 km/h.
Figure 5B:
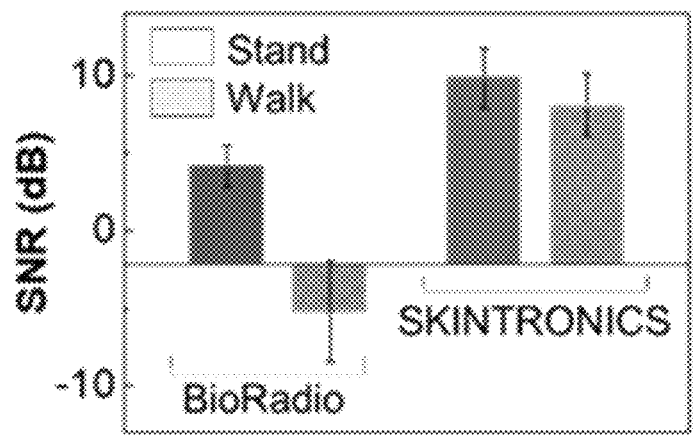
FIG. 5B provides a comparison of SNR from GSR data between two devices, capturing the effect of motion artifacts on BioRadio and negligible change on SKINTRONICS due to conformal lamination on the skin. Error bars show the standard deviation (n=5).
Figure 5C:
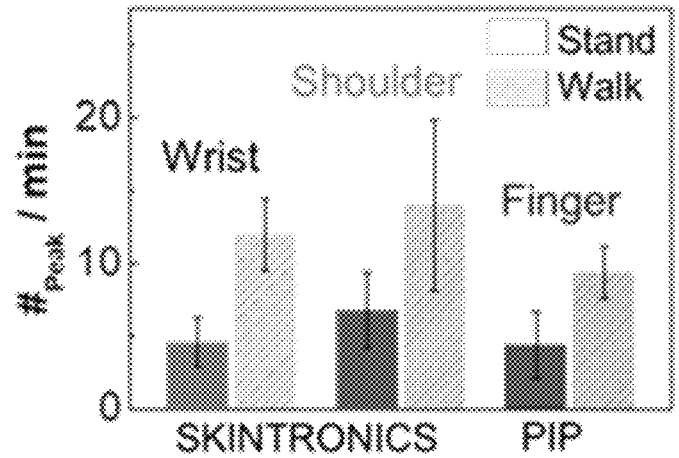
FIG. 5C provides the number of measured GSR peaks that compare two skin locations with SKINTRONICS and a reference commercial device (PIP).
Figure 5D:
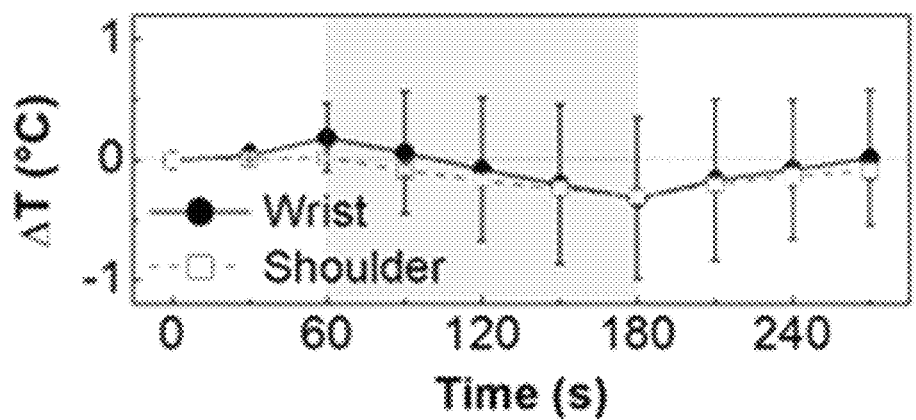
FIG. 5D provides a plo temperature variation during GSR measurement with a walking subject (n=3) wearing SKINTRONICS on the shoulder and wrist.

Existing physiological monitors are impractical for use in daily life due to various motion artifacts originating from wires, rigid electrodes, and conductive gels. SKINTRONICS, with its compact and wearable form factor as well as the soft and dry skin-electrode interface can enable continuous stress monitoring in daily life. Since walking is one of the most representative daily physical activities, here we compare how walking affects the GSR data qualities. A subject wearing both BioRadio on the fingers and SKINTRONICS on the wrist was asked to walk on a treadmill at 6 km/h. The measured GSR data, shown in FIG. 5A, captures the comparison between with and without motions, showing minimized motion artifacts from the SKINTRONICS as compared to BioRadio. Noise signal elements were separated from the phasic GSR signals by the high-pass filter with a cut-off frequency at 1 Hz and calculated for the RMS amplitude. The summarized signal-to-noise ratio (SNR) of the calculated RMS in FIG. 5B shows a minimized reduction with SKINTRONICS, compared to the significant reduction in the SNR with BioRadio. The robust GSR data qualities during user movement indicates that the stretchable gold nanomembrane electrodes maintain the seamless and conformal contact with the skin despite the absence of a conductive gel. This result further advances the concept of conformal contact into practical wearable applications by demonstrating that the stretchable layout and light-weight employed by the SKINTRONICS electronic module can enhance ambulatory data qualities, even on the wrist where constant motion is observed. FIG. 5C shows the GSR peak ratios according to the motion activity, indicating a clear deviation between the two conditions. Note that the overall number of peaks on the SKINTRONICS are larger compared to the PIP. The temperature measured by SKINTRONICS gradually decreased when the subject started to walk as shown in FIG. 5D, correlating with the excessive GSR counts during motion.

Figure 5E:
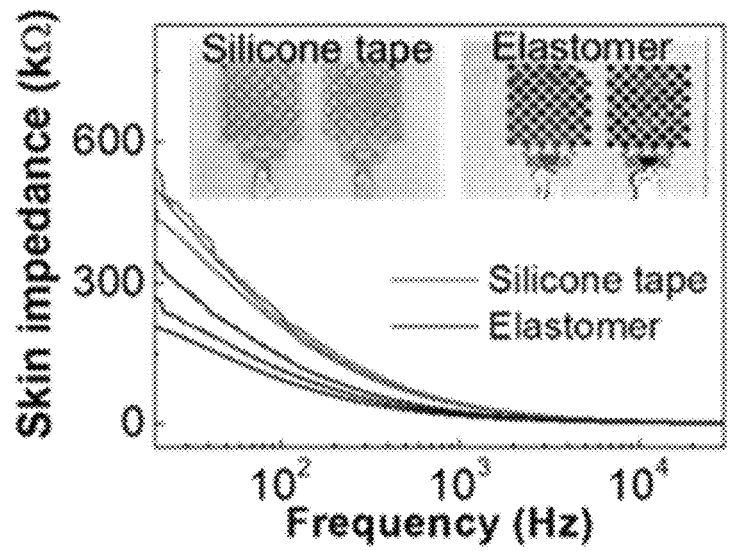
FIG. 5E provide the frequency-dependent skin impedance of SKINTRONICS with two different substrates, showing the enhanced contact by the elastomer (n=3).
Figure 5F:
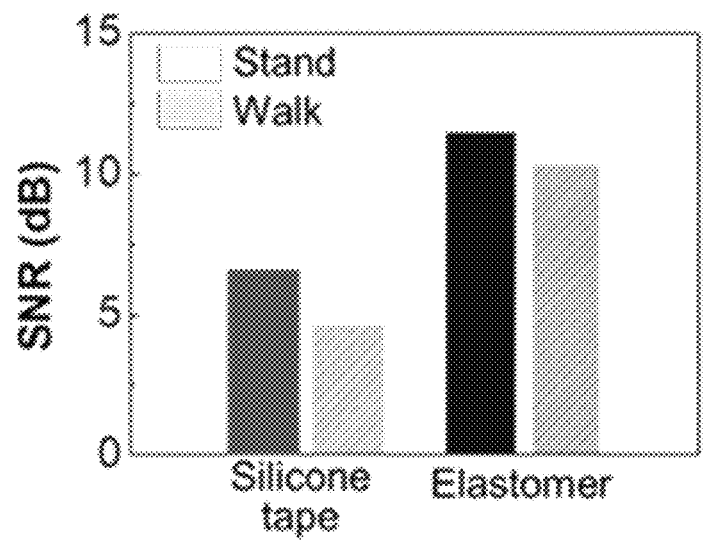
FIG. 5F provides the SNR of measured GSR data with SKINTRONICS on two types of substrates.

The contact impedance between the skin and the electrodes based on two different substrates, including a medical silicone tape (Kind Removal, 3M) and an elastomeric membrane are illustrated in FIG. 5E. The impedance-frequency plots show that the stretchable elastomer offers enhanced contact of electrodes on the skin, compared to the more rigid silicone tape. The highly stretchable elastomer allows stable electrodes and device adhesion to the skin, evidenced by both the lower contact impedance and higher SNR than the flexible silicon tape device during walking, as shown from FIG. 5F. These experimental results validate the robustness of ambulatory GSR data acquired by SKINTRONICS and verify that the low modulus elastomer substrate, stretchable designs and mechanics, and compact form factor contribute to reliable stress monitoring during walking, suggesting a significant step forward in continuous and comfortable applications.

Stress Monitoring in Daily Activities with SKINTRONICS.

Figure 6A:
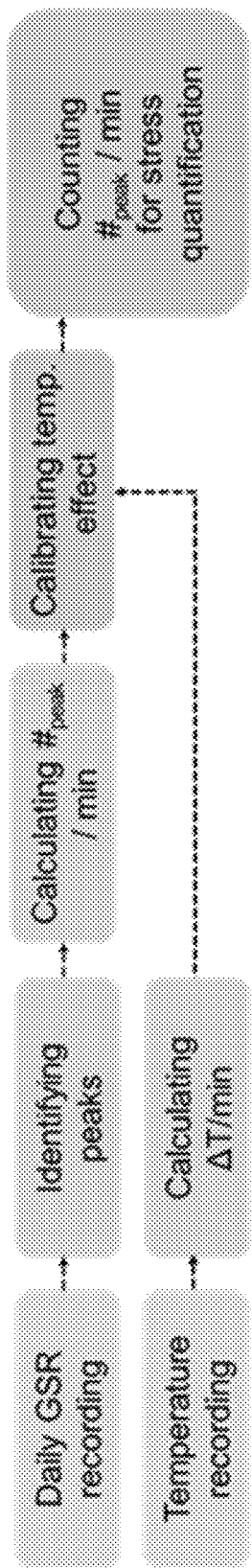
FIG. 6A provides a flow chart of a method of determining stress levels in a user of a wearable sensor, in accordance with an exemplary embodiment of the present disclosure.
Figure 6D:
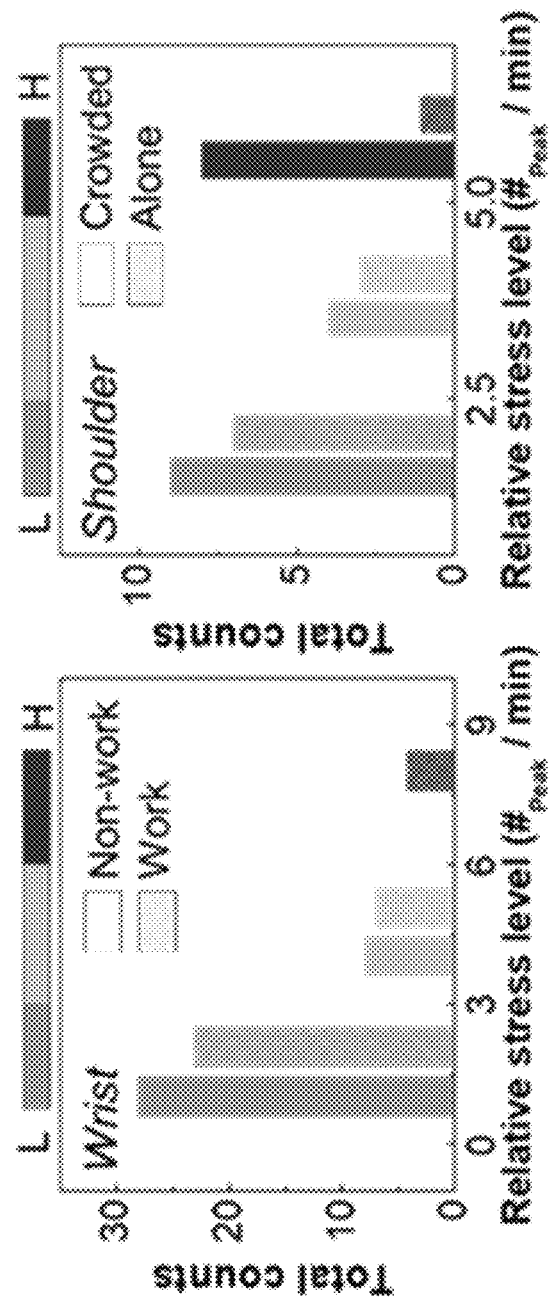
FIG. 6D provides a summary of stress quantification and relative stress level from the wrist (left) and the shoulder (right) from the measured data in FIG. 6B and FIG. 6C.
Figure 6B:
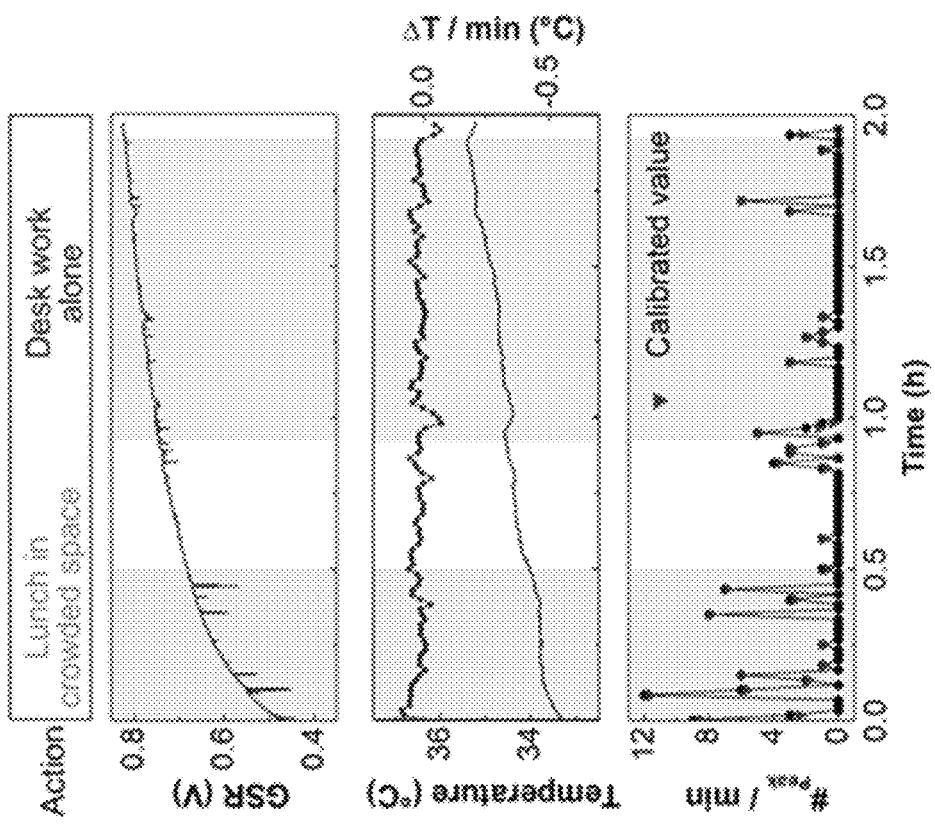
FIG. 6B provides a plot of real-time, continuous monitoring of GSR and temperature with SKINTRONICS on a subject's wrist during daily activities, including an office work with and without motions and a lunch outside.
Figure 6C:
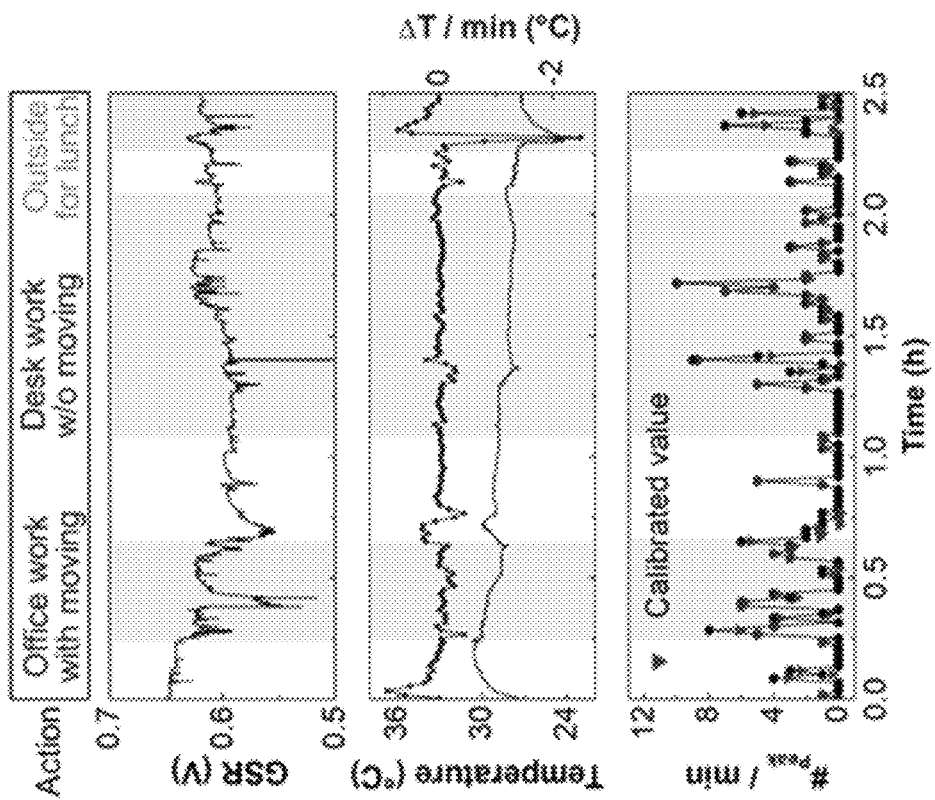
FIG. 6C provides a plot of recorded GSR and temperature data with SKINTRONICS on a subject's shoulder during daily activities of having a lunch in a crowded area and doing an office work alone.

The capability of a portable, continuous stress monitoring was demonstrated by mounting the wearable sensing device on the wrist and the shoulder. The level of stress was quantified by calculating the number of GSR peaks per minute, while temperature variation was simultaneously measured to compensate for overestimation discussed previously. The flow chart shown in FIG. 6A summarizes the overall procedure of stress quantification in daily life. FIGS. 6B and 6C present the results of measured stress levels on the wrist (FIG. 6B) and the shoulder (FIG. 6C). Grey zones in the graphs show the data when a subject was working on various tasks, while white zones mean resting states. The subject conducted several office tasks, discussion such as carrying and printing documents with colleagues, and reading research articles sitting on a chair from 10 AM to 3 PM. During lunch time, the subject walked into a different building and entered a crowded food court. Note that the dramatic temperature decrease was measured by the device during walking outside, which was calibrated for an accurate stress count. Also, the temperature variation on the shoulder was smaller than that on the wrist due to thick clothing. FIG. 6D shows the summarized data of multi-hour stress levels based on the value of #peak/min. The stress intensity is categorized by three levels via the relaxed/stressed ratio, measured in FIGS. 3F and 3G. Total counts of #peak/min at each level are calculated according to the specific daily activities. The highest stress levels (bars on the right side of the plots in FIG. 6D) are shown when a subject has multiple work-related tasks, while this subject shows the serious stress indication when exposed in a crowded space compared to being alone. Even though stress levels are subject dependent, people feel stressed during work and when surrounded by many people. Here, the wearable SKINTRONICS demonstrates the device performance as a portable, continuous stress monitor in daily life via stress level quantification. Another advantage of the exemplary soft material-enabled device is in the skin-compatibility without the use of conductive gels and aggressive tapes. In addition, the multi-layered coating of the device with polyimide and elastomer can provide the waterproof capability for a possible use during shower and/or exercise.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the United States Patent and Trademark Office and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way.

What is claimed is:

1. A method comprising:
    conformally and continuously contacting nanomembrane stretchable sensors to skin of a wearer of a wearable device, wherein the wearable device comprises:
        an elastomer layer comprising a first side and a second side;
        nanomembrane stretchable sensors having a thickness of <5 mm, an effective moduli of <50 kPa, and a weight of <7 g, the nanomembrane stretchable sensors including a galvanic skin response (GSR) sensor comprising a mesh-patterned stretchable electrode for measuring GSR of the wearer and a temperature sensor, wherein the sensors are positioned proximate the first side of the elastomer layer;
        a stretchable circuit board in electrical communication with the nanomembrane stretchable sensors via a first stretchable circuit that is configured to stretch with the elastomer layer; and a microcontroller in electrical communication with the stretchable circuit board and the nanomembrane stretchable sensors;

calibrating GSR measurements from the GSR sensor based on measured changes in temperature of the wearer detected from the temperature sensor over a predetermined threshold; and calculating a stress level of the wearer based on the calibrated GSR measurements which compensates for a fluctuation of GSR due to a temperature change of the wearer over the predetermined threshold.

2. The method of claim 1 further comprising identifying peaks in the GSR measurements that are used in the calculating of the stress level of the wearer.

3. The method of claim 2, wherein identifying peaks in the GSR measurements comprises:

filtering the GSR measurements to obtain phasic GSR signals; and performing a root mean square calculation on the phasic GSR signals.

4. The method of claim 1 further comprising:

receiving the GSR measurements of the wearer over a period of time via the GSR sensor;

receiving temperature measurements of the wearer over the period of time via the temperature sensor;

determining the measured changes in the temperature over the predetermined threshold in the temperature measurements over the period of time; and generating an output indicative of the calculated stress level.

5. The method of claim 4, wherein receiving the GSR measurements and temperature measurements comprises receiving the GSR measurements and temperature measurements at a processor of the wearable device.

6. The method of claim 5 further comprising displaying the output on one or more of the nanomembrane stretchable sensors.

7. The method of claim 4, wherein receiving the GSR measurements and temperature measurements comprises receiving the GSR measurements and temperature measurements at one or more remote devices remote from the wearable device.

8. The method of claim 7 further comprising transmitting the GSR measurements from GSR sensor to one or more of the remote devices.

9. The method of claim 8 further comprising displaying the output on one or more of the remote devices.

10. The method of claim 1, wherein calculating the stress level of the user is based on determining a number of peaks per time period in the calibrated GSR measurements.

11. The method of claim 10, wherein the stress level is proportional to the number of peaks per time period in the calibrated GSR measurements.

12. The method of claim 1 further comprising:

obtaining the GSR measurements and temperature measurements over a period of time; and displaying an output of the calculated stress level.

13. The method of claim 12, wherein displaying the output of the calculated stress level comprises displaying the output of the calculated stress level on the wearable device.

14. The method of claim 12, wherein displaying the output of the calculated stress level comprises displaying the output of the calculated stress level on a remote device.

15. The method of claim 14, wherein obtaining GSR measurements and temperature measurements comprises:

transmitting the GSR and temperature measurements from the wearable device to the remote device; and receiving the GSR and temperature measurements at the remote device.

16. The method of claim 1, wherein the conformally and continuously contacting comprises conductive gel free conformal and continuous contact of the nanomembrane stretchable sensors to the skin of the wearer of the wearable device.

* * * * *